(12) United States Patent
Burkholz et al.

(10) Patent No.: US 10,376,686 B2
(45) Date of Patent: Aug. 13, 2019

(54) ANTIMICROBIAL CAPS FOR MEDICAL CONNECTORS

(71) Applicant: Becton, Dickinson and Company, Franklin Lakes, NJ (US)

(72) Inventors: Jonathan Karl Burkholz, Salt Lake City, UT (US); Huibin Liu, West Jordan, UT (US); S. Ray Isaacson, Roy, UT (US); Weston F. Harding, Lehi, UT (US); Lawrence J. Trainer, Murray, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 25 days.

(21) Appl. No.: 14/260,027

(22) Filed: Apr. 23, 2014

(65) Prior Publication Data
US 2015/0306369 A1 Oct. 29, 2015

(51) Int. Cl.
*A61M 39/20* (2006.01)
*A61M 39/16* (2006.01)

(52) U.S. Cl.
CPC ............ *A61M 39/20* (2013.01); *A61M 39/16* (2013.01); *A61M 39/162* (2013.01); *A61M 39/165* (2013.01)

(58) Field of Classification Search
CPC .......... A61M 39/20; A61M 2039/0285; A61M 2039/0288; A61M 5/1415; A61M 5/1418; A61M 2205/0205; A61M 2025/0018; A61M 2025/0019; A61M 2025/024; A61M 39/16; A61M 39/162; A61M 39/165

USPC ................ 604/262, 264, 265, 523, 533, 539
See application file for complete search history.

(56) References Cited

U.S. PATENT DOCUMENTS

| | | |
|---|---|---|
| 1,844,023 A | 2/1932 | Terry |
| 3,223,629 A | 12/1965 | Loeffler |
| 3,695,921 A | 10/1972 | Shepherd |
| 3,867,937 A | 2/1975 | Schwartz |
| 3,986,508 A | 10/1976 | Barrington |
| 4,068,660 A | 1/1978 | Beck |
| 4,170,996 A | 10/1979 | Wu |
| 4,280,500 A | 7/1981 | Ono |
| 4,334,551 A | 6/1982 | Pfister |
| 4,339,336 A | 7/1982 | Hammond et al. |

(Continued)

FOREIGN PATENT DOCUMENTS

| | | |
|---|---|---|
| CA | 1 331 333 | 8/1994 |
| CA | 2133053 | 3/1995 |

(Continued)

OTHER PUBLICATIONS

McDonnell, G., Russell, A.D. Antiseptics and Disinfectants: Activity, Action, and Resistance. Clinical Microbiology Reviews, (1999) 12(1), pp. 149-179.

(Continued)

*Primary Examiner* — Bhisma Mehta
*Assistant Examiner* — Laura C Schell
(74) *Attorney, Agent, or Firm* — Kirton & McConkie; Craig Metcalf; Kevin Stinger

(57) ABSTRACT

The present invention relates to a cap for a medical connector. More specifically, the present invention related to an antimicrobial cap for placement over a connector, wherein various features of the antimicrobial cap maintain the connector in an antiseptic state.

10 Claims, 12 Drawing Sheets

(56) References Cited

U.S. PATENT DOCUMENTS

| | | |
|---|---|---|
| 4,387,879 A | 6/1983 | Tauschinski |
| 4,449,693 A | 5/1984 | Gereg |
| 4,512,766 A | 4/1985 | Vailancourt |
| 4,584,192 A | 4/1986 | Dell et al. |
| 4,592,920 A | 6/1986 | Murtfeldt |
| 4,603,152 A | 7/1986 | Laurin et al. |
| 4,610,674 A | 9/1986 | Suzuki |
| 4,629,743 A | 12/1986 | Hong |
| 4,629,746 A | 12/1986 | Michl et al. |
| 4,642,126 A | 2/1987 | Zador et al. |
| 4,676,782 A | 6/1987 | Yamamoto et al. |
| 4,677,143 A | 6/1987 | Laurin et al. |
| 4,716,032 A | 12/1987 | Westfall et al. |
| 4,723,948 A | 2/1988 | Clark |
| 4,758,225 A | 7/1988 | Cox |
| 4,781,703 A | 11/1988 | Walker |
| 4,798,594 A | 1/1989 | Hillstead |
| 4,805,933 A | 2/1989 | Swisher |
| 4,838,873 A | 6/1989 | Landskron |
| 4,842,591 A | 6/1989 | Luther |
| 4,846,812 A | 7/1989 | Walker |
| 4,874,377 A | 10/1989 | Newgard |
| 4,880,414 A | 11/1989 | Whipple |
| 4,895,566 A | 1/1990 | Lee |
| 4,897,427 A | 1/1990 | Barnavon et al. |
| 4,915,934 A | 4/1990 | Tomlinson |
| 4,917,668 A | 4/1990 | Haindl |
| 4,925,668 A | 5/1990 | Khan et al. |
| 4,933,178 A | 6/1990 | Capelli |
| 4,935,010 A | 6/1990 | Cox |
| 4,950,257 A | 8/1990 | Hibbs |
| 4,955,890 A | 9/1990 | Yamamoto et al. |
| 4,976,697 A | 12/1990 | Walder et al. |
| 4,985,399 A | 1/1991 | Matsuda et al. |
| 4,990,357 A | 2/1991 | Karakelle |
| 5,019,096 A | 5/1991 | Fox, Jr. et al. |
| 5,023,082 A | 6/1991 | Friedman et al. |
| 5,030,665 A * | 7/1991 | Lee .................. A61L 26/0019 522/96 |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard |
| 5,077,352 A | 12/1991 | Elton |
| 5,078,703 A * | 1/1992 | Bryant .............. A61M 25/0014 604/243 |
| 5,084,023 A | 1/1992 | Lemieux |
| 5,085,645 A | 2/1992 | Purdy |
| 5,098,410 A | 3/1992 | Kerby |
| 5,108,374 A | 4/1992 | Lemieux |
| 5,127,905 A | 7/1992 | Lemieux |
| 5,129,887 A | 7/1992 | Euteneuer et al. |
| 5,154,703 A | 10/1992 | Bonaldo |
| 5,156,596 A | 10/1992 | Balbierz |
| 5,167,647 A | 12/1992 | Wijkamp |
| 5,217,493 A | 6/1993 | Raad et al. |
| 5,226,898 A | 7/1993 | Gross |
| 5,234,410 A | 8/1993 | Graham |
| 5,242,425 A | 9/1993 | White |
| 5,256,145 A | 10/1993 | Atkinson |
| 5,290,246 A | 3/1994 | Yamamoto |
| 5,295,969 A | 3/1994 | Fischell |
| 5,330,435 A | 7/1994 | Vaillancourt |
| 5,330,449 A | 7/1994 | Prichard |
| 5,350,363 A | 9/1994 | Goode |
| 5,352,205 A | 10/1994 | Dales |
| 5,357,636 A | 10/1994 | Dresdner, Jr. et al. |
| 5,366,505 A | 11/1994 | Farber |
| 5,380,301 A | 1/1995 | Prichard |
| 5,405,323 A | 4/1995 | Rogers |
| 5,405,338 A | 4/1995 | Kranys |
| 5,456,675 A | 10/1995 | Wolbring |
| 5,456,948 A | 10/1995 | Mathisen et al. |
| 5,487,728 A | 1/1996 | Vaillancourt |
| 5,512,199 A | 4/1996 | Khan et al. |
| 5,520,666 A | 5/1996 | Choudhury |
| 5,536,258 A | 7/1996 | Folden |
| 5,540,661 A | 7/1996 | Tomisaka et al. |
| 5,547,662 A | 8/1996 | Khan et al. |
| 5,549,566 A | 8/1996 | Elias |
| 5,549,577 A | 8/1996 | Siegel |
| 5,575,769 A | 11/1996 | Vaillancourt |
| 5,589,120 A | 12/1996 | Khan et al. |
| 5,613,663 A | 3/1997 | Schmidt |
| 5,616,338 A | 4/1997 | Fox, Jr. et al. |
| 5,620,434 A | 4/1997 | Brony |
| 5,629,006 A | 5/1997 | Hoang et al. |
| 5,638,812 A | 6/1997 | Turner |
| 5,651,772 A | 7/1997 | Arnett |
| 5,653,695 A | 8/1997 | Hopkins et al. |
| 5,657,963 A | 8/1997 | Hinchliffe |
| 5,658,253 A | 8/1997 | Piontek |
| 5,676,656 A | 10/1997 | Brimhall |
| 5,688,747 A | 11/1997 | Khan |
| 5,697,915 A | 12/1997 | Lynn |
| 5,698,229 A | 12/1997 | Ohsumi et al. |
| 5,712,229 A | 1/1998 | Hopkins et al. |
| 5,716,406 A | 2/1998 | Farber |
| 5,718,678 A | 2/1998 | Fleming, III |
| 5,738,144 A | 4/1998 | Rogers |
| 5,749,861 A | 5/1998 | Guala |
| 5,763,412 A | 6/1998 | Khan et al. |
| 5,773,487 A | 6/1998 | Sokol |
| 5,806,831 A | 9/1998 | Paradis |
| 5,810,768 A | 9/1998 | Lopez |
| 5,817,069 A | 10/1998 | Arnett |
| 5,827,239 A | 10/1998 | Dillon |
| 5,830,196 A | 11/1998 | Hicks |
| 5,830,401 A | 11/1998 | Prichard |
| 5,833,674 A | 11/1998 | Turnbull |
| 5,843,046 A | 12/1998 | Motisi |
| 5,861,440 A | 1/1999 | Gohla et al. |
| 5,911,710 A | 6/1999 | Barry |
| 5,951,519 A | 9/1999 | Utterberg |
| 5,954,698 A | 9/1999 | Pike |
| 5,957,898 A | 9/1999 | Jepson |
| 5,967,490 A | 10/1999 | Pike |
| 6,039,302 A | 3/2000 | Cote, Sr. |
| 6,046,143 A | 4/2000 | Khan et al. |
| 6,051,609 A | 4/2000 | Yu et al. |
| 6,068,622 A | 5/2000 | Sater |
| 6,074,379 A | 6/2000 | Prichard |
| 6,077,244 A | 6/2000 | Botich |
| 6,102,890 A | 8/2000 | Stivland |
| 6,117,108 A | 8/2000 | Woehr |
| 6,120,784 A | 9/2000 | Snyder, Jr. |
| 6,127,320 A | 10/2000 | van Ooij et al. |
| 6,156,054 A | 12/2000 | Zadno-Azizi |
| 6,165,168 A | 12/2000 | Russo |
| 6,171,287 B1 | 1/2001 | Lynn |
| 6,217,566 B1 | 4/2001 | Ju |
| 6,228,073 B1 | 5/2001 | Noone |
| 6,242,526 B1 | 6/2001 | Siddiqui et al. |
| 6,245,098 B1 | 6/2001 | Feeser |
| 6,248,811 B1 | 6/2001 | Ottersbach et al. |
| 6,273,404 B1 | 8/2001 | Holman |
| 6,273,869 B1 | 8/2001 | Vaillancourt |
| 6,322,847 B1 | 11/2001 | Zhong et al. |
| 6,326,417 B1 | 12/2001 | Jia |
| 6,332,874 B1 | 12/2001 | Eliasen |
| 6,337,357 B1 | 1/2002 | Fukunishi et al. |
| 6,344,218 B1 | 2/2002 | Dodd et al. |
| 6,353,041 B1 | 3/2002 | Qian |
| 6,387,075 B1 | 5/2002 | Stivland |
| 6,413,539 B1 | 7/2002 | Shalaby |
| 6,426,373 B1 | 7/2002 | Stange |
| 6,475,434 B1 | 11/2002 | Darouiche |
| 6,485,473 B1 | 11/2002 | Lynn |
| 6,488,942 B1 | 12/2002 | Ingemann |
| 6,492,445 B2 | 12/2002 | Siddiqui et al. |
| 6,503,353 B1 | 1/2003 | Peterson |
| 6,511,462 B1 | 1/2003 | Itou |
| 6,544,214 B1 | 4/2003 | Utterberg |
| 6,575,958 B1 | 6/2003 | Happ |

(56) References Cited

U.S. PATENT DOCUMENTS

| | | |
|---|---|---|
| 6,575,960 B2 | 6/2003 | Becker |
| 6,576,633 B1 | 6/2003 | Young et al. |
| 6,579,221 B1 | 6/2003 | Peterson |
| 6,579,539 B2 | 6/2003 | Lawson et al. |
| 6,595,981 B2 | 7/2003 | Huet |
| 6,663,614 B1 | 12/2003 | Carter |
| 6,699,221 B2 | 3/2004 | Vaillancourt |
| 6,719,726 B2 | 4/2004 | Meng |
| 6,719,991 B2 | 4/2004 | Darouiche et al. |
| 6,723,350 B2 | 4/2004 | Burrell et al. |
| 6,740,063 B2 | 5/2004 | Lynn |
| 6,808,161 B1 | 10/2004 | Hishikawa |
| 6,843,784 B2 | 1/2005 | Modak et al. |
| 6,846,846 B2 | 1/2005 | Modak et al. |
| 6,861,060 B1 | 3/2005 | Luriya et al. |
| 6,883,778 B1 | 4/2005 | Newton |
| 6,887,270 B2 | 5/2005 | Miller et al. |
| 6,893,456 B2 | 5/2005 | Lumauig |
| 6,896,889 B2 | 5/2005 | Chevalier et al. |
| 7,008,404 B2 | 3/2006 | Nakajima |
| 7,074,839 B2 | 7/2006 | Fansler et al. |
| 7,098,256 B2 | 8/2006 | Ong et al. |
| 7,115,183 B2 | 10/2006 | Larson |
| 7,179,849 B2 | 2/2007 | Terry |
| 7,198,800 B1 | 4/2007 | Ko |
| 7,232,428 B1 | 6/2007 | Inukai |
| 7,232,540 B2 | 6/2007 | Gould et al. |
| 7,261,925 B2 | 8/2007 | Nesbitt |
| 7,268,165 B2 | 9/2007 | Greten et al. |
| 7,347,839 B2 | 3/2008 | Hiejima |
| 7,374,798 B2 | 5/2008 | Choo et al. |
| 7,396,346 B2 | 7/2008 | Nakajima |
| 7,407,707 B2 | 8/2008 | Gould et al. |
| 7,462,401 B2 | 12/2008 | Halfyard et al. |
| 7,470,254 B2 | 12/2008 | Basta |
| 7,494,339 B2 | 2/2009 | Dias et al. |
| 7,498,367 B2 | 3/2009 | Qian |
| 7,514,477 B2 | 4/2009 | Klare et al. |
| 7,608,082 B2 | 10/2009 | Cuevas |
| 7,704,935 B1 | 4/2010 | Davis et al. |
| 7,736,339 B2 | 6/2010 | Woehr |
| 7,816,434 B2 | 10/2010 | Hackbarth et al. |
| 7,871,649 B2 | 1/2011 | Modak et al. |
| 7,874,467 B2 | 1/2011 | Pardes |
| 7,914,494 B2 | 3/2011 | Hiejima |
| 7,981,475 B2 | 7/2011 | Takahashi |
| 8,034,454 B2 | 10/2011 | Terry |
| 8,034,455 B2 | 10/2011 | Wang et al. |
| 8,067,402 B2 | 11/2011 | Whiteford et al. |
| 8,133,423 B2 | 3/2012 | Tang |
| 8,227,050 B1 | 7/2012 | O'Neil |
| 8,231,602 B2 | 7/2012 | Anderson |
| 8,263,102 B2 | 9/2012 | Labrecque et al. |
| 8,268,381 B2 | 9/2012 | Whiteford et al. |
| 8,343,523 B2 | 1/2013 | Toreki |
| 8,343,525 B2 | 1/2013 | Davis et al. |
| 8,353,876 B2 | 1/2013 | Suwito |
| 8,357,119 B2 | 1/2013 | Stout |
| 8,388,583 B2 | 3/2013 | Stout et al. |
| 8,414,547 B2 | 4/2013 | DiFiore et al. |
| 8,512,294 B2 | 8/2013 | Ou-Yang |
| 8,622,995 B2 | 1/2014 | Ziebol et al. |
| 8,622,996 B2 | 1/2014 | Ziebol et al. |
| 8,691,887 B2 | 4/2014 | Ou-Yang |
| 8,728,030 B2 | 5/2014 | Woehr |
| 8,840,927 B2 | 9/2014 | Ditizio |
| 9,078,441 B2 | 7/2015 | Raad |
| 9,138,252 B2 | 9/2015 | Bierman |
| 2001/0010016 A1 | 7/2001 | Modak et al. |
| 2001/0016589 A1 | 8/2001 | Modak et al. |
| 2001/0018095 A1 | 8/2001 | Shlenker |
| 2001/0032006 A1 | 10/2001 | Griffin, III et al. |
| 2001/0049519 A1 | 12/2001 | Holman |
| 2001/0053895 A1 | 12/2001 | Vaillancourt |
| 2001/0056133 A1 | 12/2001 | Montgomery et al. |
| 2002/0009436 A1 | 1/2002 | Doyle et al. |
| 2002/0022660 A1 | 2/2002 | Jampani et al. |
| 2002/0028751 A1 | 3/2002 | Lokkesmoe et al. |
| 2002/0037260 A1 | 3/2002 | Budny et al. |
| 2002/0040092 A1 | 4/2002 | Siddiqui et al. |
| 2002/0064858 A1 | 5/2002 | Yacoby-Zeevi |
| 2002/0091424 A1 | 7/2002 | Biel |
| 2002/0119111 A1 | 8/2002 | Kilgour et al. |
| 2002/0133124 A1 | 9/2002 | Leinsing et al. |
| 2002/0144705 A1 | 10/2002 | Brattesani et al. |
| 2003/0023208 A1 | 1/2003 | Osypka |
| 2003/0060804 A1 | 3/2003 | Vaillancourt |
| 2003/0068667 A1 | 4/2003 | Olson |
| 2003/0072781 A1 | 4/2003 | Pelerin |
| 2003/0105143 A1 | 6/2003 | Ammendola et al. |
| 2003/0119932 A1 | 6/2003 | Al-Akhdar et al. |
| 2003/0134783 A1 | 7/2003 | Harshey et al. |
| 2003/0144362 A1 | 7/2003 | Utterberg |
| 2003/0147932 A1 | 8/2003 | Nun et al. |
| 2003/0162839 A1 | 8/2003 | Symington et al. |
| 2003/0170308 A1 | 9/2003 | Clean et al. |
| 2003/0176848 A1 | 9/2003 | Gibson et al. |
| 2003/0206875 A1 | 11/2003 | Budny et al. |
| 2003/0215433 A1 | 11/2003 | Kokai-Kun et al. |
| 2003/0224032 A1 | 12/2003 | Read et al. |
| 2004/0013574 A1 | 1/2004 | Conway |
| 2004/0013703 A1 | 1/2004 | Ralph |
| 2004/0014864 A1 | 1/2004 | Milic et al. |
| 2004/0039349 A1 | 2/2004 | Modak et al. |
| 2004/0058829 A1 | 3/2004 | Hei et al. |
| 2004/0062592 A1 | 4/2004 | Shekalim |
| 2004/0109852 A1 | 6/2004 | Xu |
| 2004/0115477 A1 | 6/2004 | Nesbitt |
| 2004/0132164 A1 | 7/2004 | Doyle et al. |
| 2004/0180829 A1 | 9/2004 | Bassler et al. |
| 2004/0185296 A1 | 9/2004 | Mazzanti |
| 2004/0230162 A1* | 11/2004 | Tan .................. A61L 2/16 604/171 |
| 2004/0234475 A1 | 11/2004 | Lannibois-Drean et al. |
| 2005/0008671 A1 | 1/2005 | Van Antwerp |
| 2005/0048005 A1 | 3/2005 | Stockel |
| 2005/0048124 A1 | 3/2005 | Sarangapani |
| 2005/0059731 A1 | 3/2005 | Albrecht et al. |
| 2005/0080158 A1 | 4/2005 | Ong et al. |
| 2005/0100580 A1 | 5/2005 | Osborne et al. |
| 2005/0118239 A1 | 6/2005 | Sabesan |
| 2005/0124970 A1 | 6/2005 | Kunin |
| 2005/0131356 A1 | 6/2005 | Ash et al. |
| 2005/0143286 A1 | 6/2005 | Singh et al. |
| 2005/0147525 A1* | 7/2005 | Bousquet ............ A61L 2/18 422/28 |
| 2005/0148928 A1 | 7/2005 | Molina |
| 2005/0158253 A1 | 7/2005 | Budny et al. |
| 2005/0176905 A1 | 8/2005 | Moon et al. |
| 2005/0209581 A1 | 9/2005 | Butts |
| 2005/0209583 A1 | 9/2005 | Powers |
| 2005/0233950 A1 | 10/2005 | Madhyastha |
| 2005/0265931 A1 | 12/2005 | Qian |
| 2006/0024372 A1 | 2/2006 | Utterberg et al. |
| 2006/0051385 A1 | 3/2006 | Scholz |
| 2006/0064159 A1 | 3/2006 | Porter |
| 2006/0163515 A1 | 7/2006 | Ruschke |
| 2006/0165751 A1 | 7/2006 | Chudzik et al. |
| 2006/0165903 A1 | 7/2006 | Mazzanti |
| 2006/0177477 A1 | 8/2006 | Ash |
| 2006/0239954 A1 | 10/2006 | Sancho |
| 2006/0258780 A1 | 11/2006 | Chaussade et al. |
| 2006/0259012 A1 | 11/2006 | Propp |
| 2006/0281663 A1 | 12/2006 | Asmus |
| 2007/0000407 A1 | 1/2007 | Leong |
| 2007/0083157 A1 | 4/2007 | Belley |
| 2007/0083162 A1 | 4/2007 | O'Reagan |
| 2007/0093762 A1* | 4/2007 | Utterberg .......... A61M 39/02 604/256 |
| 2007/0112112 A1 | 5/2007 | Kerschner et al. |
| 2007/0112146 A1 | 5/2007 | Falk et al. |
| 2007/0129690 A1 | 6/2007 | Rosenblatt |
| 2007/0141524 A1 | 6/2007 | Brennan et al. |
| 2007/0160547 A1 | 7/2007 | Duffy et al. |

(56) References Cited

U.S. PATENT DOCUMENTS

| | | |
|---|---|---|
| 2007/0166344 A1 | 7/2007 | Qu et al. |
| 2007/0202177 A1 | 8/2007 | Hoang |
| 2007/0203574 A1 | 8/2007 | McGrath et al. |
| 2007/0225179 A1 | 9/2007 | Schutz et al. |
| 2007/0233007 A1 | 10/2007 | Adams |
| 2007/0275101 A1 | 11/2007 | Lu et al. |
| 2007/0281198 A1 | 12/2007 | Lousenberg |
| 2008/0026026 A1 | 1/2008 | Lu et al. |
| 2008/0027410 A1 | 1/2008 | Harding |
| 2008/0033371 A1* | 2/2008 | Updegraff ............ A61M 39/162 604/263 |
| 2008/0039796 A1 | 2/2008 | Nakajima |
| 2008/0051737 A1 | 2/2008 | Paul et al. |
| 2008/0075761 A1 | 3/2008 | Modak et al. |
| 2008/0103487 A1 | 5/2008 | Miyasaka |
| 2008/0108944 A1 | 5/2008 | Woehr |
| 2008/0119789 A1 | 5/2008 | Kaemmerer |
| 2008/0161763 A1* | 7/2008 | Harding ............... A61M 39/045 604/265 |
| 2008/0182921 A1 | 7/2008 | Suh et al. |
| 2008/0194707 A1 | 8/2008 | Potter |
| 2008/0319387 A1 | 12/2008 | Amisar et al. |
| 2009/0012220 A1 | 1/2009 | Yamane et al. |
| 2009/0036768 A1 | 2/2009 | Seehusen et al. |
| 2009/0062766 A1 | 3/2009 | Howlett et al. |
| 2009/0101152 A1 | 4/2009 | Burk et al. |
| 2009/0110844 A1 | 4/2009 | Platzer et al. |
| 2009/0114327 A1 | 5/2009 | Breunig |
| 2009/0117164 A1 | 5/2009 | Toreki et al. |
| 2009/0125118 A1 | 5/2009 | Gong |
| 2009/0157007 A1 | 6/2009 | McKinnon |
| 2009/0162530 A1 | 6/2009 | Nesbitt |
| 2009/0176907 A1 | 7/2009 | Subramanian et al. |
| 2009/0188559 A1 | 7/2009 | Nesbitt |
| 2009/0220739 A1 | 9/2009 | Chougule |
| 2009/0226541 A1 | 9/2009 | Scholz et al. |
| 2009/0281525 A1 | 11/2009 | Harding |
| 2009/0317435 A1 | 12/2009 | Vandesteeg et al. |
| 2009/0324666 A1 | 12/2009 | Krongauz et al. |
| 2009/0324738 A1 | 12/2009 | Krongauz |
| 2010/0015200 A1 | 1/2010 | McClain |
| 2010/0024648 A1 | 2/2010 | Breault |
| 2010/0069854 A1 | 3/2010 | Okoh |
| 2010/0106102 A1* | 4/2010 | Ziebol .................... A61L 2/186 604/265 |
| 2010/0106103 A1 | 4/2010 | Ziebol |
| 2010/0135949 A1 | 6/2010 | Ou-Yang |
| 2010/0136209 A1 | 6/2010 | Ou-Yang et al. |
| 2010/0137379 A1 | 6/2010 | Ou-Yang |
| 2010/0137472 A1 | 6/2010 | Ou-Yang |
| 2010/0200017 A1 | 8/2010 | Kerr et al. |
| 2010/0204648 A1 | 8/2010 | Stout et al. |
| 2010/0204675 A1 | 8/2010 | Woehr |
| 2010/0222746 A1 | 9/2010 | Burkholz |
| 2011/0009831 A1 | 1/2011 | Burkholz et al. |
| 2011/0044850 A1* | 2/2011 | Solomon ............ A61M 39/162 422/28 |
| 2011/0065798 A1 | 3/2011 | Hoang et al. |
| 2011/0146680 A1 | 6/2011 | Conway |
| 2011/0150958 A1 | 6/2011 | Davis et al. |
| 2011/0160662 A1 | 6/2011 | Stout |
| 2011/0160663 A1 | 6/2011 | Stout et al. |
| 2011/0218529 A1 | 9/2011 | Garcia |
| 2011/0301553 A1 | 12/2011 | Goral et al. |
| 2011/0319825 A1 | 12/2011 | Goral et al. |
| 2012/0016318 A1* | 1/2012 | Hoang .................. A61M 39/16 604/288.01 |
| 2012/0078203 A1* | 3/2012 | Gaube .................. A61M 39/16 604/288.03 |
| 2012/0083750 A1 | 4/2012 | Sansoucy |
| 2012/0103448 A1 | 5/2012 | Hopf |
| 2012/0111368 A1* | 5/2012 | Rahimy ............... A61M 39/162 134/22.1 |
| 2013/0090607 A1 | 4/2013 | McKinnon |
| 2013/0165868 A1 | 6/2013 | Isaacson |
| 2013/0171030 A1* | 7/2013 | Ferlic ..................... A61M 39/20 422/119 |
| 2013/0196079 A1 | 8/2013 | Schwalm |
| 2013/0197485 A1* | 8/2013 | Gardner ............... A61M 39/162 604/533 |
| 2013/0204231 A1 | 8/2013 | Ziebol et al. |
| 2013/0245568 A1 | 9/2013 | Kerr |
| 2013/0274686 A1* | 10/2013 | Ziebol ................ A61M 25/0017 604/265 |
| 2013/0310764 A1 | 11/2013 | Burkholz |
| 2013/0330387 A1 | 12/2013 | Ou-Yang |
| 2016/0008517 A1 | 1/2016 | Burkholz |
| 2017/0095596 A1* | 4/2017 | Petrak ................. A61C 13/0018 |

FOREIGN PATENT DOCUMENTS

| | | |
|---|---|---|
| CA | 2133053 A1 | 3/1995 |
| CN | 1187598 | 7/1998 |
| CN | 1187598 A | 7/1998 |
| CN | 1526771 A | 9/2004 |
| CN | 101353545 A | 1/2009 |
| CN | 102070983 A | 5/2011 |
| CN | 102497894 | 6/2012 |
| DE | 3314640 | 11/1983 |
| DE | 3913392 | 10/1990 |
| DE | 4011867 A1 | 10/1991 |
| DE | 202009009602 | 12/2009 |
| EP | 0 036 294 A2 | 9/1981 |
| EP | 0070087 | 1/1983 |
| EP | 0070087 B1 | 1/1983 |
| EP | 0227230 | 7/1987 |
| EP | 0 338 418 A1 | 10/1989 |
| EP | 0370997 | 5/1990 |
| EP | 0370997 A2 | 5/1990 |
| EP | 0 379 271 | 7/1990 |
| EP | 0379271 B1 | 7/1990 |
| EP | 0 396 431 A2 | 11/1990 |
| EP | 0 414 997 A1 | 3/1991 |
| EP | 484092 | 5/1992 |
| EP | 0778337 A2 | 6/1997 |
| EP | 778337 | 11/1997 |
| EP | 992252 | 4/2000 |
| EP | 0992252 B1 | 4/2000 |
| EP | 1466645 B1 | 10/2004 |
| EP | 1679043 | 7/2006 |
| EP | 1679043 B1 | 7/2006 |
| EP | 2868722 | 5/2015 |
| JP | 05-277434 | 10/1993 |
| JP | 07-051651 | 2/1995 |
| JP | H07-47435 A | 2/1995 |
| JP | 08-209064 | 8/1996 |
| JP | H08-311373 A | 11/1996 |
| JP | 09-151262 | 6/1997 |
| JP | 09-157548 | 6/1997 |
| JP | H09-176677 A | 7/1997 |
| JP | 09-324135 | 12/1997 |
| JP | H10-231 A | 1/1998 |
| JP | H11-322560 A | 11/1999 |
| JP | 2000-178475 A | 6/2000 |
| JP | 2000-264803 A | 9/2000 |
| JP | 2001-072438 A | 3/2001 |
| JP | 2002-282762 | 10/2002 |
| JP | 2003-342402 | 12/2003 |
| JP | 2004-043669 A | 2/2004 |
| JP | 2005-028209 A | 2/2005 |
| JP | 2005-515838 A | 6/2005 |
| JP | 2005-520912 A | 7/2005 |
| JP | 2007-016096 A | 1/2007 |
| JP | 2008-533051 A | 8/2008 |
| JP | 2009-527356 | 7/2009 |
| JP | 2009-528360 | 8/2009 |
| JP | 2009-544454 | 12/2009 |
| JP | 2010-174075 | 8/2010 |
| JP | 2010-536836 A | 12/2010 |
| JP | 2012-510559 | 5/2012 |
| JP | 2012-532681 A | 12/2012 |
| JP | 2013-505062 | 2/2013 |
| JP | 2013540486 | 11/2013 |

(56) References Cited

FOREIGN PATENT DOCUMENTS

| | | |
|---|---|---|
| JP | 2015-519303 | 7/2015 |
| KR | 20020066429 A | 8/2002 |
| KR | 20080039460 | 5/2008 |
| KR | 20080039460 A | 5/2008 |
| WO | 82/00413 | 2/1982 |
| WO | 94/22522 | 10/1994 |
| WO | 95/21648 | 8/1995 |
| WO | 96/16690 | 6/1996 |
| WO | 96/40359 | 12/1996 |
| WO | 98/58690 | 12/1998 |
| WO | 98/58989 | 12/1998 |
| WO | 99/16498 | 4/1999 |
| WO | 99/32168 | 7/1999 |
| WO | 99/34849 | 7/1999 |
| WO | 99/36490 | 7/1999 |
| WO | 99/43971 | 9/1999 |
| WO | 99/44654 | 9/1999 |
| WO | 00/12171 | 3/2000 |
| WO | 00/66189 | 11/2000 |
| WO | 00/74743 | 12/2000 |
| WO | 01/47592 | 7/2001 |
| WO | 01/95862 | 12/2001 |
| WO | 2004/071568 | 8/2004 |
| WO | 2004/108091 A2 | 12/2004 |
| WO | 2005/037340 | 4/2005 |
| WO | 2006/012446 | 2/2006 |
| WO | 2006056482 A1 | 6/2006 |
| WO | 2006074666 A2 | 7/2006 |
| WO | 2006/088288 A1 | 8/2006 |
| WO | 2006/099358 A2 | 9/2006 |
| WO | 2006/099359 | 9/2006 |
| WO | 2006/100442 | 9/2006 |
| WO | 2007/064835 A2 | 6/2007 |
| WO | 2007095576 A2 | 8/2007 |
| WO | 2007/100653 A2 | 9/2007 |
| WO | 2007/100776 A2 | 9/2007 |
| WO | 2008/014438 A2 | 1/2008 |
| WO | 2008/014447 A2 | 1/2008 |
| WO | 2008/031601 A1 | 3/2008 |
| WO | 2008/045761 A2 | 4/2008 |
| WO | 2008/052790 | 5/2008 |
| WO | 2008/128896 A2 | 10/2008 |
| WO | 2008/132045 A2 | 11/2008 |
| WO | 2009/012336 | 1/2009 |
| WO | 2009/055949 | 5/2009 |
| WO | 2009/070227 A1 | 6/2009 |
| WO | 2009/114833 | 9/2009 |
| WO | WO2010034470 * | 4/2010 |
| WO | 2010/093791 | 8/2010 |
| WO | 2011/005951 | 1/2011 |
| WO | 2011/034675 A2 | 3/2011 |
| WO | 2011/048204 | 4/2011 |
| WO | 2011/118680 | 9/2011 |
| WO | WO 2011/118680 | 9/2011 |
| WO | 2012/036916 A1 | 3/2012 |
| WO | 2013/009998 | 1/2013 |
| WO | 2013/134421 | 9/2013 |
| WO | 2014/031774 | 2/2014 |
| WO | 2015/133281 | 9/2015 |

OTHER PUBLICATIONS

"ComfortCoat Hydrophilic Coating," DSM in Medical, http://www.dsm.com/en_US/medical/public/home/pages/product-coating-comfortcoat.jsp, Updated Jan. 11, 2013, Printed Apr. 22, 2013.

"Lubricent—Lubricious Hydrophillic Coatings for Medical Devices," Harland Medical Systems, http://www.harlandmedical.com/index.php/materials/lubricent.html, pp. 1-2, Printed Apr. 22, 2013.

"UV & EB Cure," Xiper Innovations, Inc., http://xiperinnovations.com/uv_eb_cure, Printed Apr. 22, 2013.

Cabot Corporation, "Using Silicas and Aluminas in Coatings,", www.cabot-corp.com/Silicas-And-Aluminas/Coatings, downloaded from the Internet on Apr. 26, 2011.

Gama Healthcare, ClinellAlcoholic 2% Chlorhexidine, http://www.gamahealthcare.com/clinellaca2c.html, pp. 1-3, Nov. 7, 2008.

Sage Products, Inc., Preoperative Skin Preparation for the Surgical Patient, http://www.sageproducts.com/products/skin-prep.cfm, 1 page, Oct. 31, 2008.

Sage Products, Inc., Address Multi-Drug Resistant Organisms on the Skin with Early Preop Prep, http://www.sageproducts.com/products/ssi-prevention.cfm, 1 page, Oct. 31, 2008.

Sage Products, Inc., Preoperative Skin Preparation and Perioperative Oral Care for the Short-Term Ventilated Patient, http://www.sageproducts.com/products/ssi-vap-prevention.cfm, 1 page, Oct. 31, 2008.

Enturia, ChloraPrep, http://www.enturia.com/products/chloraPrep/chloraPrep-product.html, pp. 1-3, Oct. 31, 2008.

Anusavice KJ, Zhang N-Z, Shen C. Controlled Release of Chlorhexidine from UDMA-TEGDMA Resin, Journal of dental research, 2006;85(10); 950-954.

Ciba Irgacure 500 data sheet from Ciba Specialty Chamicals, online, retrieved on [Dec. 13, 2015]. Retrieved from internet <url://http://www.conquimica.com/wp-content/uploads/2015/06/ft-irgacure-500.pdf>.

Elson Silva, PhD, "Respecting Hydrology Science in the Patenting System," pp. 1-7, Jan. 13, 2011.

Anusavice K.J., Zhang Z.-Z., Shen C., Controlled Release of Chlorhexidine from UDMA-TEGDMA Resin, Journal of Dental Research, 2006;85(10); 950-954.

Elson Silva, PhD, "Respecting Hydrology Science in the Patenting System," pp. 1-7, Jun. 1, 2011.

* cited by examiner

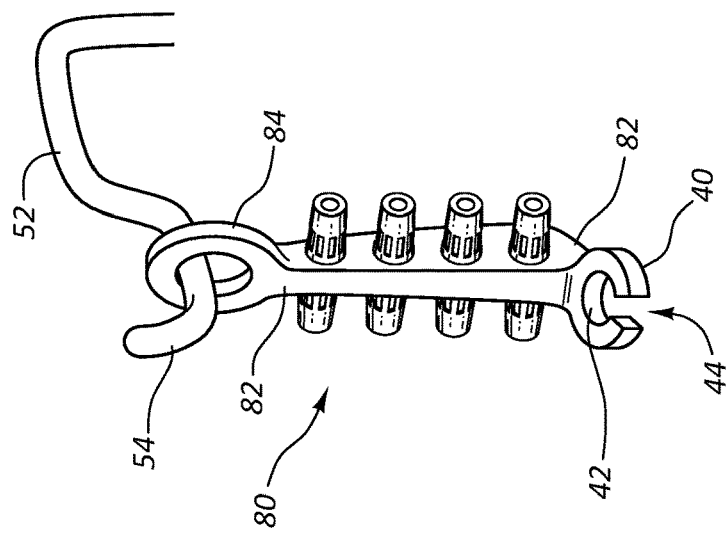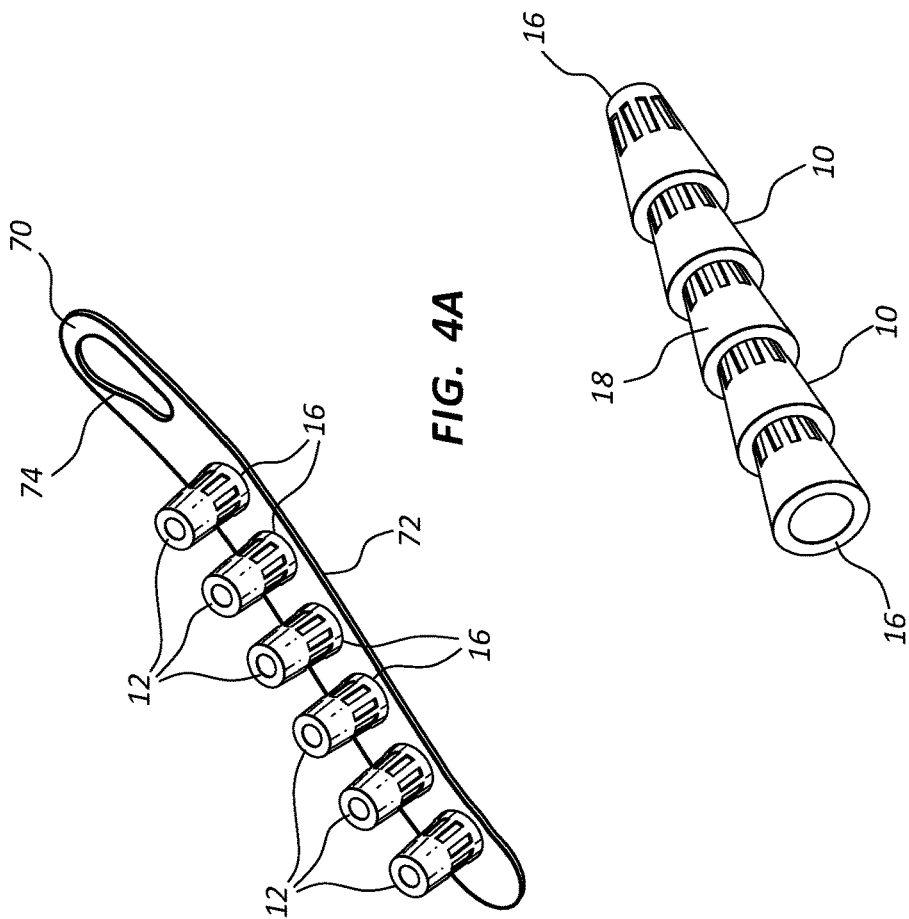

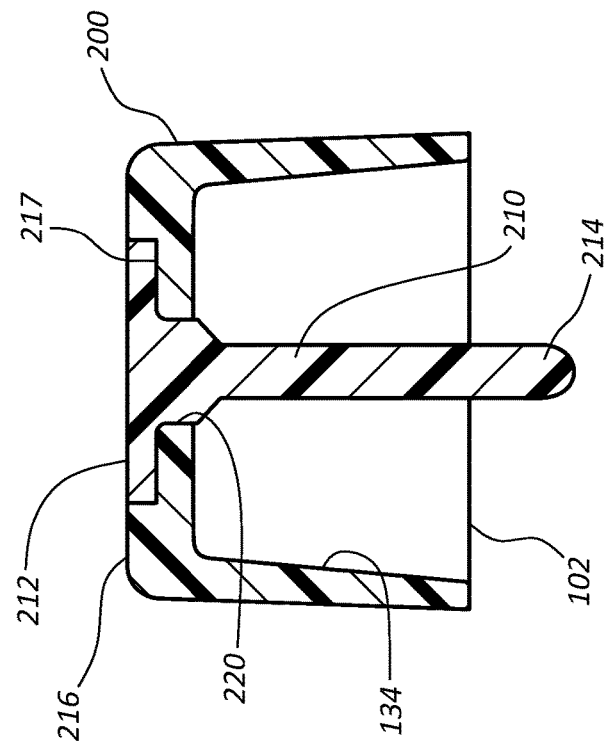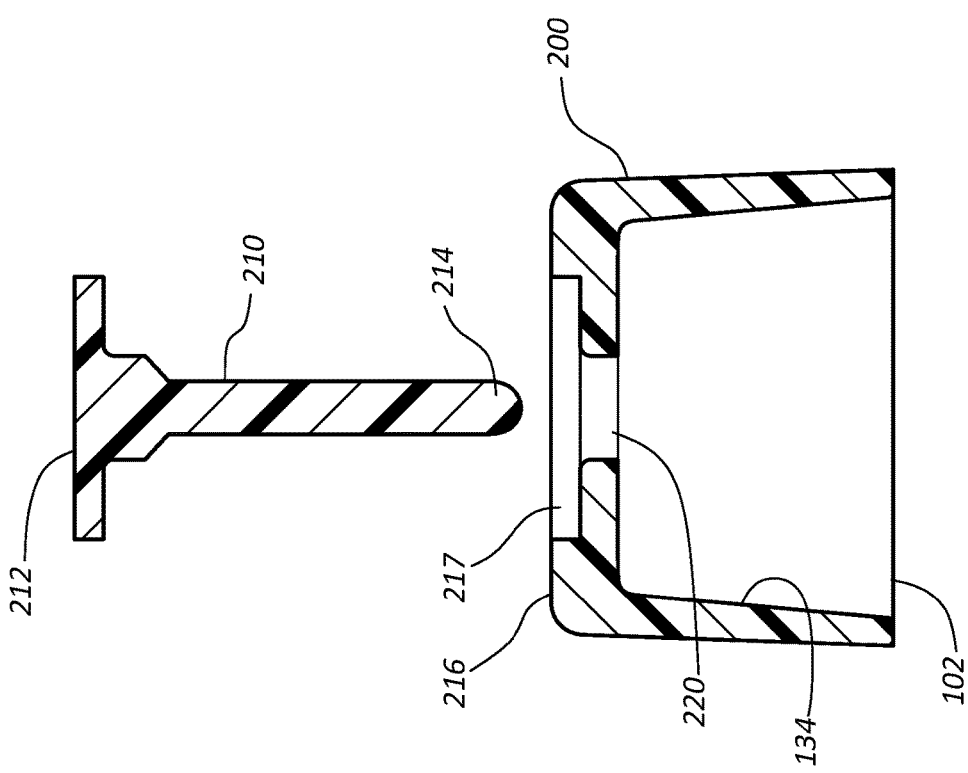

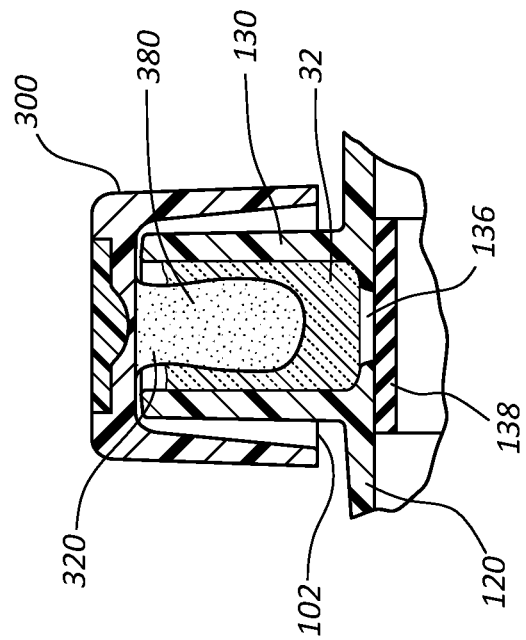
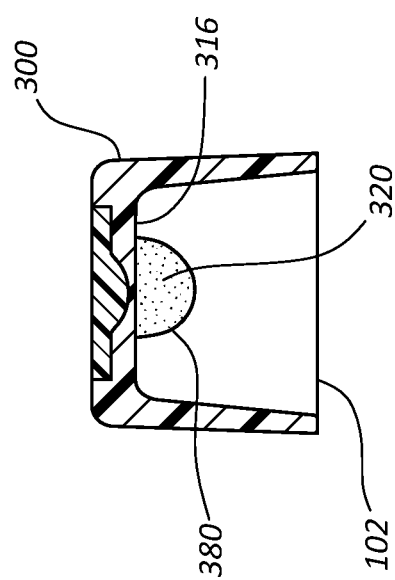
FIG. 10B
FIG. 10A

ANTIMICROBIAL CAPS FOR MEDICAL CONNECTORS

BACKGROUND OF THE INVENTION

Infusion therapy generally involves the administration of a medication intravenously. When performing a typical infusion therapy, one or more infusion therapy device (e.g. tubing sets) are used. Oftentimes, during infusion therapy, the end of the tubing set is left exposed to non-sterile surfaces such as when a syringe is removed from a male Luer end of the tubing set. For example, when the end of the tubing set is exposed, the patient or nurse may touch the end, or the end may come in contact with non-sterile bedding, table, or floor surfaces.

Although it is required to clean the hub or needleless connector end of the tubing set, it is not required to clean the other end which is typically a male Luer. Disinfection caps are increasingly being used to disinfect the ends of infusion therapy devices such as needleless connectors, IV sets, or short extension tubing. Such caps generally include foam soaked with alcohol which contacts surfaces of the port when the cap is connected to the port. Various problems exist when using these caps. For example, the alcohol soaked foam only contacts exterior surfaces of the access port. Also, once a cap is placed on a port, the alcohol in the cap evaporates quickly. Further, use of alcohol often results in alcohol being forced into the IV line.

Further, some types of female Luer connectors trap liquids which are incapable of being effectively treated by conventional disinfection caps. For example, side ports on a catheter adapter are commonly used as a quick access for IV medications or fluid injection into an IV line, or into the patient's bloodstream, for quick effects, especially in emergency situations. The port may be accessed multiple times during the entire use of a catheter; sometimes in excess of seven days. Contaminated Luer access devices, such as a syringe, when connected to the port may transfer microorganisms the side wall and bottom of the side port. This may result in microorganism growth and colonization inside the port, which poses a risk of infection for the patient. Currently available disinfections caps are not able to effectively disinfect these surfaces.

Thus, while methods and systems currently exist for disinfecting needleless connectors, challenges still exist. Accordingly, it would be an improvement in the art to augment or replace current techniques with the systems and methods discussed herein.

BRIEF SUMMARY OF THE INVENTION

The present invention relates to a cap for a medical connector. More specifically, the present invention related to an antimicrobial cap for placement over a connector, wherein various features of the antimicrobial cap maintain the connector in an antiseptic state.

Some implementations of the present invention provide an antimicrobial cap having an inner surface on which is disposed a dry, non-bonded antimicrobial material. Upon exposure to a residual fluid, the dry, non-bonded antimicrobial material is quickly dissolved, thereby forming an antimicrobial solution within the closed volume of the cap. The antimicrobial solution contacts the inner surface of the cap and the outer surfaces of a connector inserted within the interior of the cap.

Other implementations of the present invention provide various clip features on the outer surface of an antimicrobial cap, wherein the clip feature allow the cap to be attached to a section of IV tubing, or an IV pole to prevent the cap from contacting an undesired surface, such as the ground. Various structures are further provided for storing and dispensing the antimicrobial caps to a clinician.

Some implementations of the present invention further comprise an antimicrobial cap having an antimicrobial plug. The antimicrobial plug extends outwardly from the inner, base surface of the cap and extends into an interior volume of a connector having an interior space into which the plug may extend. The antimicrobial plug may comprise various shapes and configurations to maximize surface area without compromising the function of the cap and/or the connector.

In some instances, an antimicrobial cap is provided having a removable/disposable antimicrobial plug. The removable plug is inserted into the cap via a hole provided in the base of the cap, opposite the opening of the cap. The plug may be inserted, used, and then removed to maintain adequate antimicrobial effect.

Some implementations of the instant invention comprise an antimicrobial growth material that is attached to the inner surface of the cap's base. The growth material comprises an antimicrobial agent or coating that is eluted from the material when contacted by a residual fluid. The growth material is dehydrated and swells or grows when exposed to a liquid.

Further, some implementations of the instant invention comprise a cap having an inner surface on which is disposed an antimicrobial lubricant. The antimicrobial lubricant is transferred to the outer and inner surfaces of a connector when the cap is placed thereon. Upon removal of the cap, the antimicrobial lubricant remains on the cap and connector surfaces, thereby imparting an antimicrobial effect.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 4, shown in parts A-C, shows perspective views of various storage and distributions methods and devices in accordance with various representative embodiments of the present invention.

FIG. 10, shown in parts A and B, shows cross-section views of an antimicrobial growing material in accordance with a representative embodiment of the present invention.

DETAILED DESCRIPTION OF THE INVENTION

The present invention relates to a cap for a medical connector. More specifically, the present invention related to an antimicrobial cap for placement over a connector, wherein various features of the antimicrobial cap maintain the connector in an antiseptic state.

As used herein the term "connector" is understood to include any structure that is part of an intravenous device that is capable of making a connection with a secondary intravenous device. Non-limiting examples of connectors in accordance with the present invention include needleless connectors, male Luer connectors, female Luer connectors, side port valves, y-port valves, port valves, and other similar structures.

Figure 1:
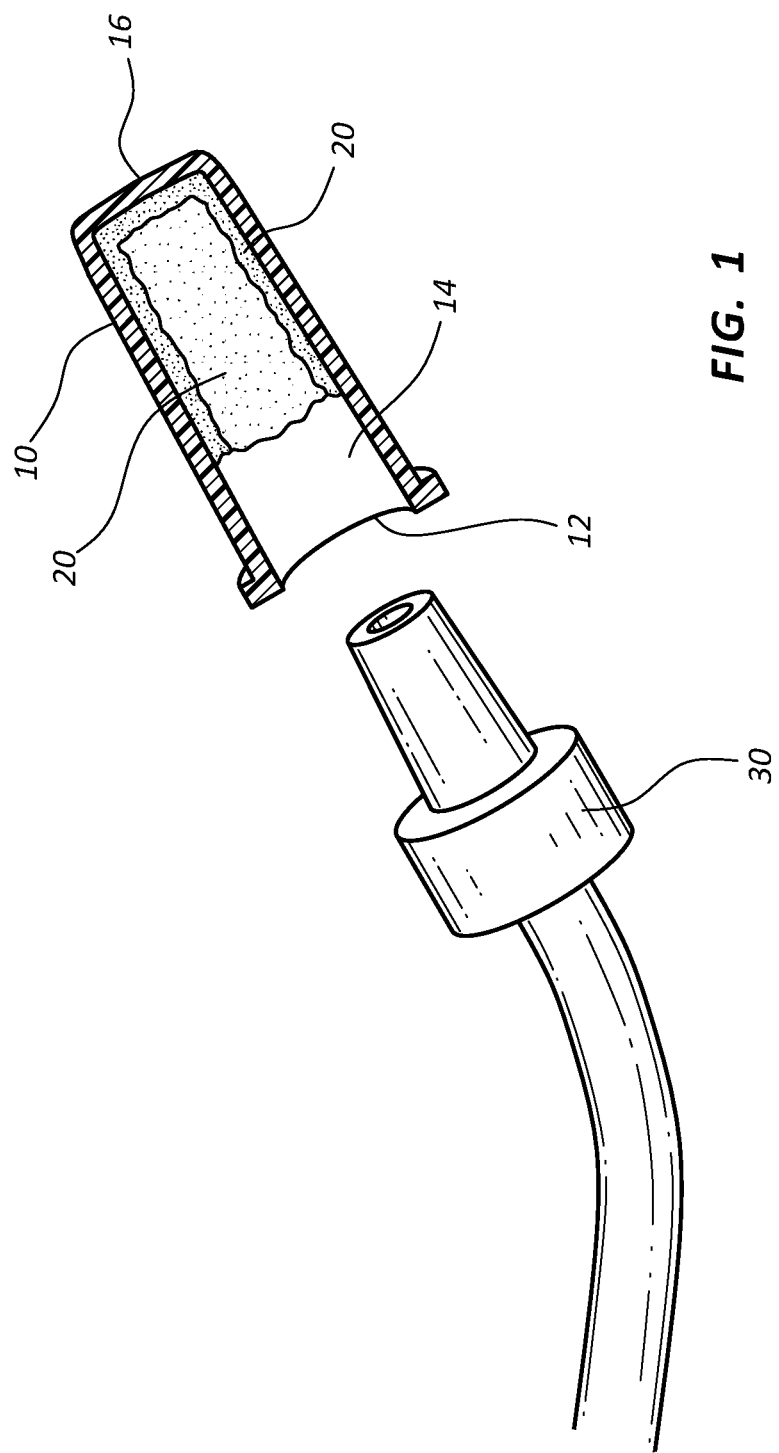
FIG. 1 shows a cross-section view of an antimicrobial cap in accordance with a representative embodiment of the present invention.

Referring now to FIG. 1, an antimicrobial cap 10 is shown. Antimicrobial cap 10 generally comprises a polymer material that is safe for use with fluid and chemicals common to infusion procedures. For example, in some instances cap 10 comprises a poly vinyl chloride material. Cap 10 comprises an opening 12 having a diameter sufficient to receive a connector 30. In some instances, connector 30 comprises a positive surface that may be inserted through opening 12 of cap 10. For example, in some instances connector 30 comprises a male Luer connector. In other instances connector 30 comprises a syringe tip. Further, in some instances connector 30 comprises a side port or y-port of a catheter adapter. In other instances connector 30 comprises a catheter adapter, a section of IV tubing, or a catheter.

In some embodiments, cap 10 receives connector 30 via a threaded connection. For example, in some instances cap 10 comprises a set of internal or external threads that are threadedly engaged by a complementary set of threads located on the connector. In other instances, cap 10 receives connector 30 via a friction or interference fit.

Antimicrobial cap 10 further comprises an inner surface 14 defining a volume sufficient to receive connector 30. Inner surface 14 is generally tubular, however in some instances inner surface 14 tapers inwardly from opening 12 to the cap's base 16. Inner surface 14 may include any geometry or shape as may be desired. An interior surface of the base 16 may form a flat planar surface across the entire region between the outer sidewall(s) of the cap 10.

The volume of cap 10 comprises the interior space of cap 10 extending from opening 12 to base 16. The volume is generally selected to admit placement of connector 30 within cap 10 for the purpose of maintaining cap 10 in an antiseptic condition. Accordingly, antimicrobial cap 10 further comprises a quantity of antimicrobial material 20 applied to inner surface 14. Antimicrobial material 20 may comprise any type or form of antimicrobial material that is safe for use in accordance with the teachings of the present invention. For example, in some instances antimicrobial material 20 is selected from a group consisting of chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element.

In some embodiments, antimicrobial material 20 comprises a dry, non-bonded coating that is applied to inner surface 14 by a known method. For instance, in some embodiments antimicrobial material 20 is applied to inner surface 14 by spraying, dipping or brushing. In other instances, antimicrobial material 20 comprises a UV cured polymer matrix in which an antimicrobial agent is uniformly dispersed. The antimicrobial agent is not chemically bound to the polymer matrix, and therefore is capable of being eluted out of the matrix when the matrix is exposed to, or wetted by a residual fluid.

Figure 2:
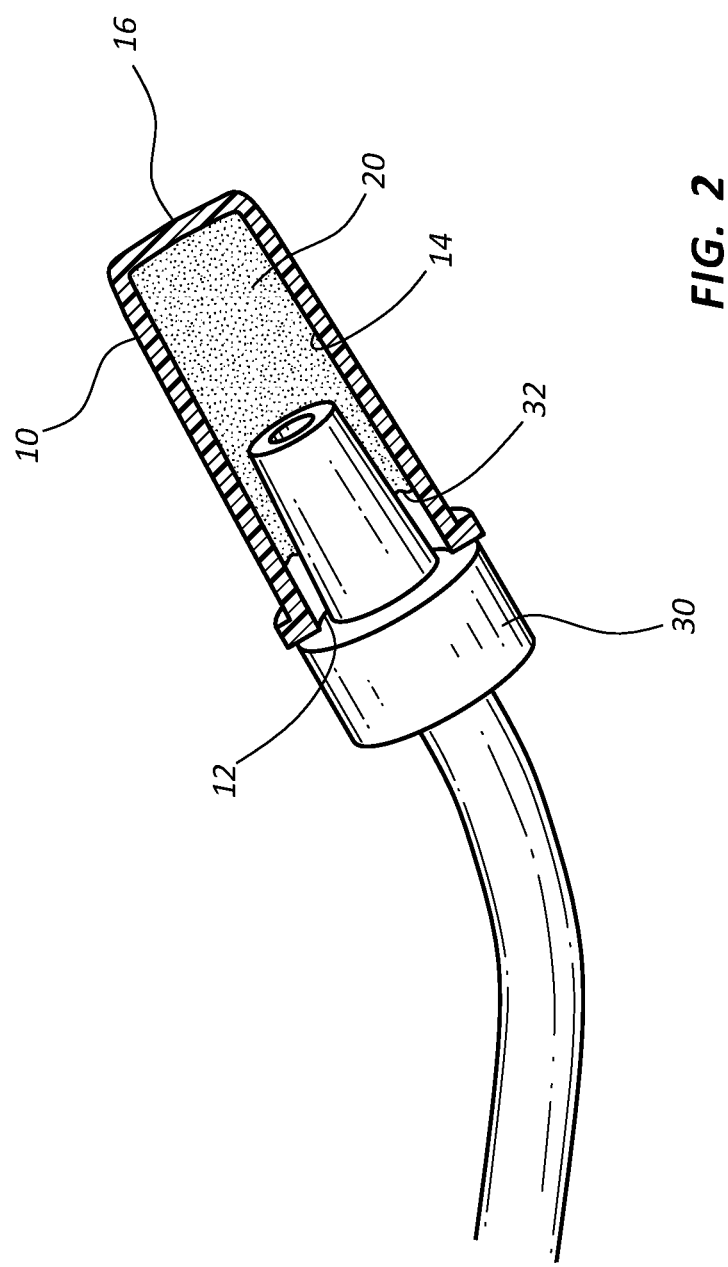
FIG. 2 shows a cross-section view of an antimicrobial cap and a perspective view of a connector inserted therein in accordance with a representative embodiment of the present invention.

When cap 10 is placed onto connector 30, connector 30 reduces the volume of cap 10. Once secured together, connector 30 and antimicrobial cap 10 form a closed volume between the interconnected devices. Upon exposure to a residual fluid 32 from connector 30, the dry, non-bonded antimicrobial material 20 is rapidly dissolved by residual fluid 32, thereby forming an antimicrobial solution with the residual fluid 32 within the closed volume, as shown in FIG. 2. The antimicrobial solution is contained within the closed volume and is exposed to all of the surfaces of needleless adapter 30 and inner surface 14 positioned within the closed volume.

As discussed above, in some instances antimicrobial material 20 comprises a UV cured, hydrophilic polymer material that forms a matrix comprising a plurality of microscopic interstices in which an antimicrobial agent is evenly dispersed (not shown). Upon exposure to residual fluid 32, the polymer matrix is softened and penetrated by the residual fluid. The antimicrobial agent within the polymer matrix is eluted out of the matrix and into the residual fluid to form an antimicrobial solution have a desired final concentration within the closed volume. Examples of suitable polymer materials are provided in U.S. patent application Ser. Nos. 12/397,760, 11/829,010, 12/476,997, 12/490,235, and 12/831,880, each of which is incorporated herein in their entireties.

Generally, a quantity or amount of antimicrobial material 20 is applied to inner surface so that upon being dissolved in residual fluid 32 within the closed volume, an antimicrobial solution is provided having a minimum concentration required to have sufficient antimicrobial efficacy within the closed volume. In some instances, a predetermined quantity or amount of antimicrobial material 20 is applied to inner surface 14 to provide a final concentration from approximately 0.005% w/w to approximately 25% w/w. Thus, the quantity or amount of antimicrobial material 20 is determined based upon the calculated closed volume of antimicrobial cap 10 and connector 30.

For example, if the volume of antimicrobial cap 10 is 1 $cm^3$, and the volume of the portion of connector 30 that is inserted into cap 10 is 0.75 $cm^3$, then the calculated closed volume of antimicrobial cap 10 is 0.25 $cm^3$. Thus, the maximum possible volume of residual fluid 32 within the closed volume is 0.25 $cm^3$. Accordingly, to achieve a final, desired concentration of antimicrobial material within the antimicrobial solution from approximately 0.005% w/w to approximately 25% w/w (within the closed volume), approximately 12.6 µg to approximately 83.3 mg of antimicrobial material 20 will need to be applied to inner surface 14.

Residual fluid 32 may comprise any fluid or combination of fluids common to infusion therapy procedures. For example, in some embodiments residual fluid 32 comprises blood, a medicament, water, saline, urine, or combinations thereof. In some instances, a residual fluid 32 leaks into antimicrobial cap 10 after connector 30 has been inserted into cap 10. In other instance, a residual fluid 32 is present on connector 30 prior to being inserted into cap 10. Further, in some instances a residual fluid 32 is present in antimicrobial cap 10 prior to connector 30 being inserted therein.

Following use of antimicrobial cap 10, cap 10 is removed from connector 30 and is disposed. In some instances, antimicrobial cap 10 is reused multiple times prior to being disposed. For example, in some instances cap 10 is applied to connector 30 after connector 30 is removed from a separate connector (not shown). Prior to reconnecting connector 30 to the separate connector, antimicrobial cap 10 is again removed from connector 30, and reapplied following removal of connector 30 from the separate connector.

Figure 3C:
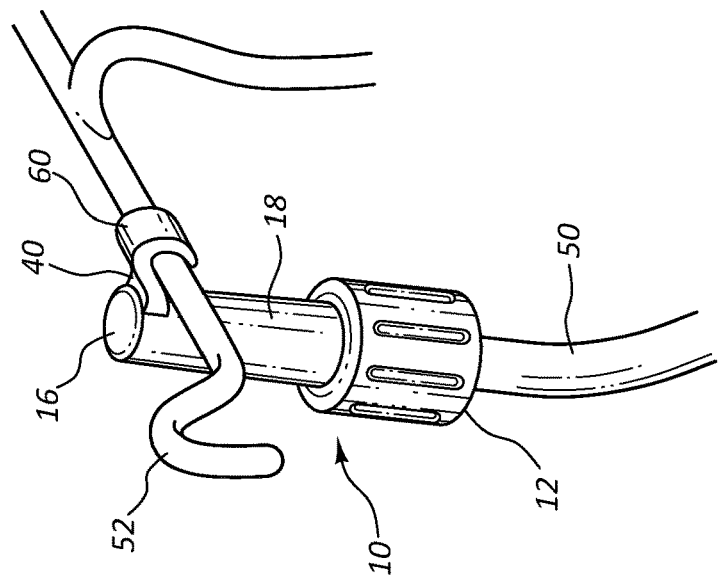
FIG. 3, shown in parts A-C, shows perspective views of various clip features in accordance with various representative embodiment of the present invention.
Figure 3B:
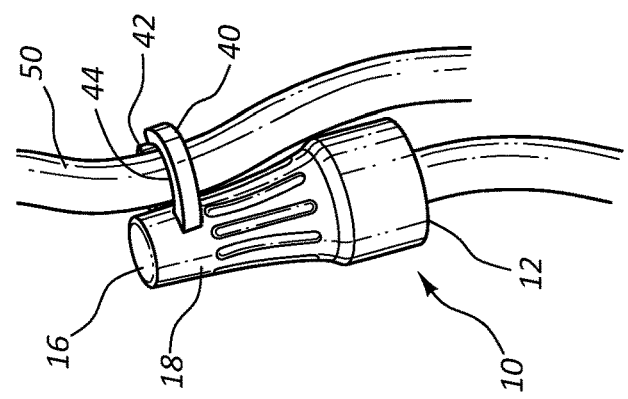
Figure 3A:
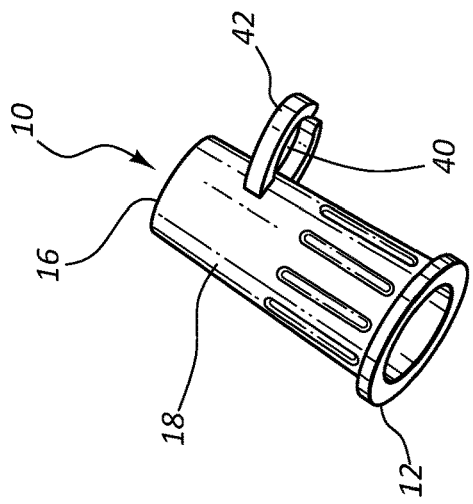

In some instances, the exterior 18 of antimicrobial cap 10 further comprises a clip 40 having a surface 42 for receiving at least one of an IV line, and an IV pole to maintain a desired position of antimicrobial cap 10, as shown in FIGS. 3A-3C. In some instances, clip 40 comprises a pair of opposed arms forming an aperture 44 having a diameter sufficient to receive the outer diameter of a section of IV tubing 50, as shown in FIG. 3B. In other instances, clip 40 comprises a single hook 60 having a hooked surface for compatibly receiving an IV pole 52, as shown in FIG. 3C. Thus, in some embodiments antimicrobial cap 10 is coupled to a connector 30 and then coupled to a section of IV tubing 50 or an IV pole 52 via clip 40 to prevent undesired contact with a floor or other undesirable surface.

Referring now to FIG. 4, the present invention further comprises various devices for storing and dispensing antimicrobial cap 10. For example, in some instances a disposable strip 70 is provided having an elongated surface 72 on which the base 16 surfaces of multiple caps 10 is temporarily adhered with a weak adhesive, as shown in FIG. 4A. Since antimicrobial material 20 is provided in a dry form, openings 12 may be oriented outwardly from surface 72 without requiring a foil or polymer cover. Strip 70 further comprises a hole 74 designed to receive a hook portion of an IV pole, whereby to suspend strip 70 in a convenient location for a clinician.

In other instances, the exterior surfaces 18 of antimicrobial caps 10 are tapered inwardly from opening 12 to base 16, wherein the diameter of base 16 is less than the diameter of opening 12, as shown in FIG. 4B. Thus, base 16 may be fitted into opening 12 of an adjacent cap 10 by interference fit to form a stacked configuration. Again, the dry form of antimicrobial material 20 does not require a foil or polymer cover for openings 12, thereby allowing the stacked configuration for storage and dispensing purposes.

Further, in some instances a caddy 80 is provided having opposing surfaces 82 on which the base surfaces 16 of multiple caps 10 are temporarily adhered with a weak adhesive, as shown in FIG. 4C. Since antimicrobial material 20 is provided in a dry form, openings 12 may be oriented outwardly from surfaces 82 without requiring covers for opening 12. Caddy 80 further comprises a hole 84 designed to receive a hook portion 54 of an IV pole, whereby to suspend caddy 80 in a convenient location for a clinician. Caddy 80 further comprises a clip 40 having a surface 42 and aperture 44 for receiving a section of IV tubing.

Referring now generally to FIGS. 5-11C, in some instances antimicrobial cap 100 is hingedly coupled to a catheter adapter 120 and configured to provide a physical barrier for a connector comprising a side port 130. Although shown as being hingedly integrated onto a catheter adapter, the features of antimicrobial cap 100 discussed in connection with these embodiments may be implemented into any style or form of antimicrobial cap configured to receive any type or style of connector.

Figure 5A:
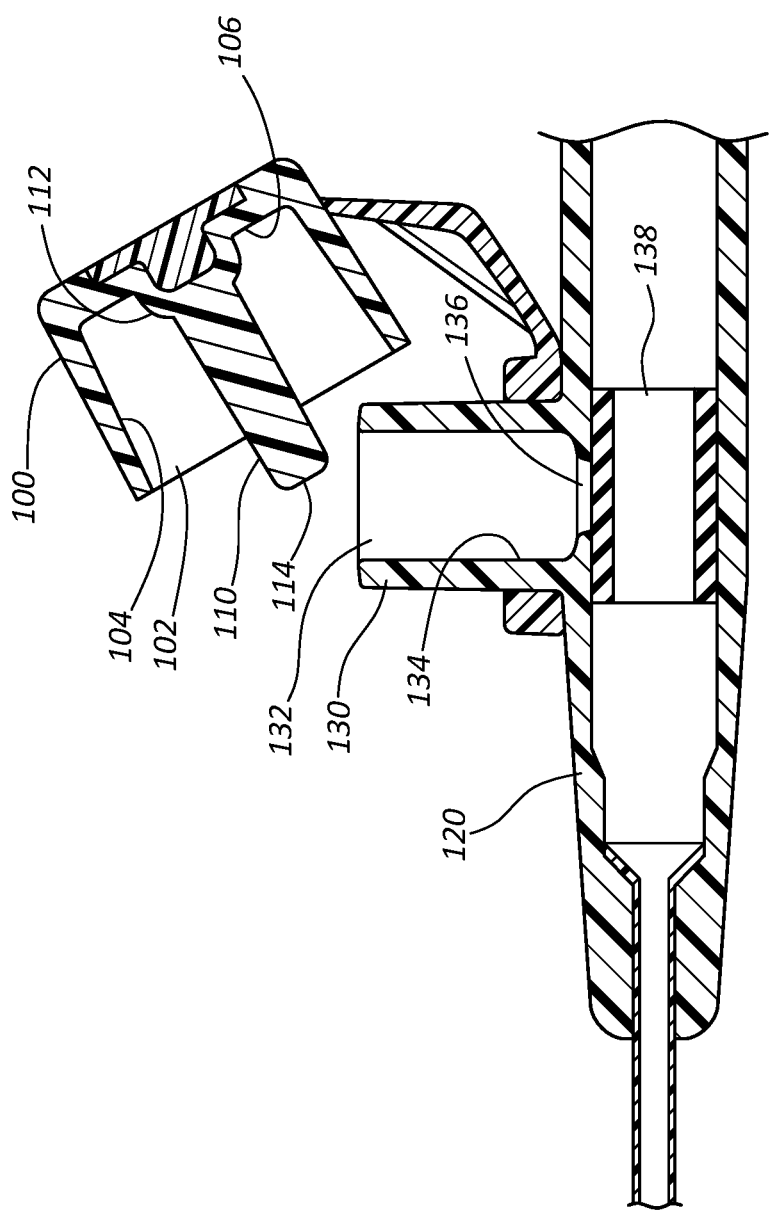
FIG. 5, shown in parts A and B, shows cross-section views of an antimicrobial cap having an antimicrobial plug in accordance with a representative embodiment of the present invention.
Figure 5B:
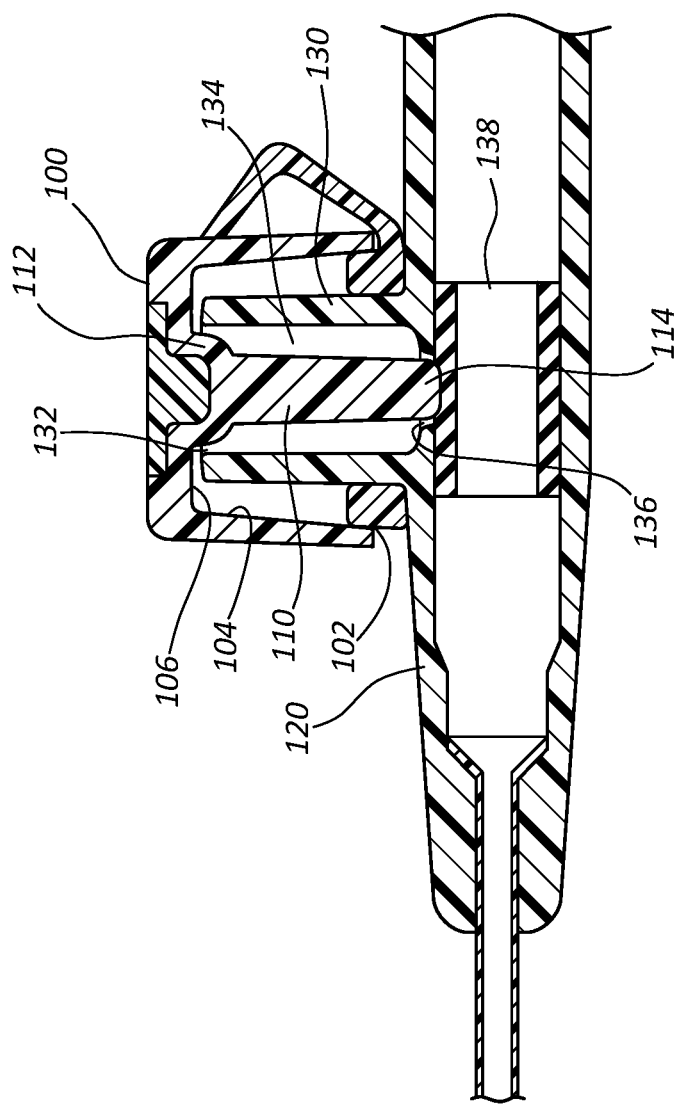

With specific reference to FIGS. 5A and 5B, in some instances antimicrobial cap 100 comprises an opening 102 having a diameter sufficient to receive side port 130. Cap 100 further comprises an inner surface 104 defining a volume sufficient to receive side port 130.

Side port 130 comprises an opening or aperture 132, an internal volume 134, and a bottom 136. In some instances, internal volume 134 may further comprise a unique internal geometry, as discussed below. Side port 130 further comprises a port valve 138 that forms a defeatable seal between side port 130 and an interior lumen of catheter adapter 120. Upon injecting a fluid into side port 130, port valve 138 is temporarily defeated to break the seal and permit the injected fluid to bypass port valve 138 and enter the interior lumen of catheter adapter 120. Following the injection, a small aliquot of residual fluid is typically left in internal volume 134, and may be susceptible to microbial contamination. This residual fluid typically pools and gathers at the bottom 136 of side port 130 and contacts the outer surface of port valve 138. However, larger volumes of residual fluid may contact additional surfaces of internal volume 134, and may even fill or substantially fill internal volume 134. The port valve 138 may selectively block fluid communication between the catheter adapter 120 and the side port 130 through the bottom of the side port 130.

Antimicrobial cap 100 further comprises an antimicrobial plug 110. Antimicrobial plug 110 generally comprises an antimicrobial material or coating that is readily dissolved or eluted when plug 110 contacts a residual fluid in internal volume 134. In some instances, antimicrobial plug 110 comprises a UV cured, hydrophilic material in which is evenly dispersed an antimicrobial agent, as described above. In other instances, plug 110 is comprised of a solid antimicrobial material. In other instances, plug 110 comprises a polymer tube having an antimicrobial coating.

Antimicrobial plug 110 may comprise any form or shape that is compatible with the teachings of the present invention. For example, in some instances plug 110 comprises a tubular shape. In other instances plug 110 comprises a rod. Further, in some instances antimicrobial plug 110 comprises a non-linear shape or design, as shown and discussed in connection with FIGS. 8B-9, below.

Antimicrobial plug 110 comprises a proximal end 112 that is attached to base 106 of cap 100, and further comprises a distal end 114 that extends outwardly from base 106. Plug 110 comprises a length and diameter sufficient to be inserted through aperture 132 and positioned within internal volume 134 such that distal end 114 is positioned in proximity with bottom 136 when cap 100 is coupled to side port 130, as shown in FIG. 5B. The distal end 114 of the antimicrobial plug 110 may extend through the bottom of the side port 130 to abut the port valve 138 when the cap 100 is secured to the side port 130.

The length and diameter of plug 110 is selected to maximize the surface area of plug 110 without compromising the ability of cap 100 to be hingedly closed over side port 130. In some instances plug 110 comprises an outer diameter of approximately 0.076 inches and a functional height of approximately 0.338 inches.

Figure 6A:
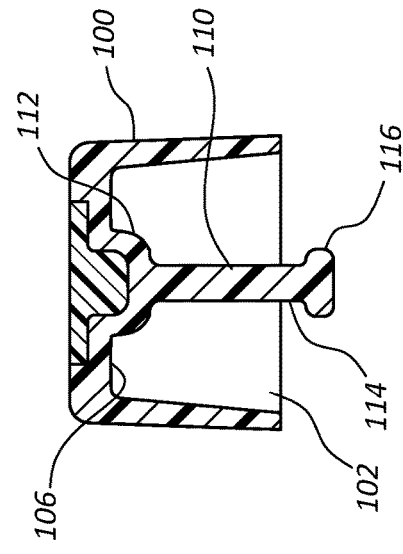
FIG. 6, shown in parts A and B, shows a cross-section view of a curved antimicrobial plug in accordance with a representative embodiment of the present invention.
Figure 6B:
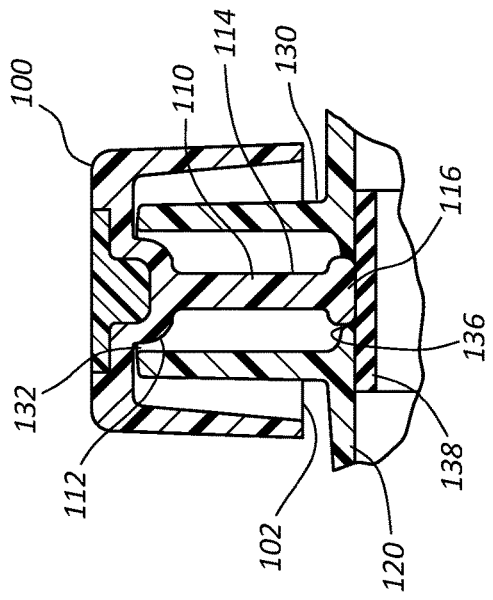

In some instances it may be desirable to increase the surface area of antimicrobial plug 110 while still maintaining the functionality of the hinged connection. Accordingly, in some embodiments antimicrobial plug 110 is curved, as shown in FIGS. 6A and 6B. The curved configuration of plug 110 increases the overall length of plug 110 yet prevents contact between distal end 114 and aperture 132 upon hingedly closing cap 100 onto side port 130. Thus, the overall surface area of plug 110 is increased without disturbing the normal function of the hinged cap.

Figure 7A:
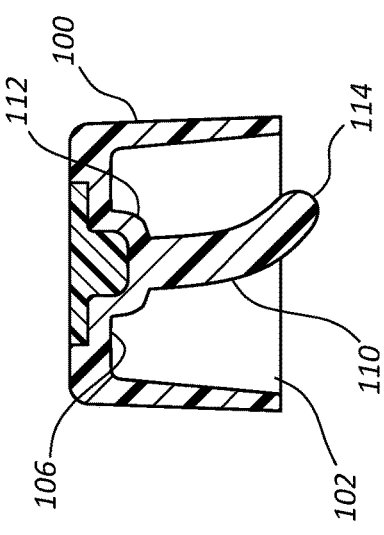
FIG. 7, shown in parts A and B, shows a cross-section view of an antimicrobial plug having a terminal end disc in accordance with a representative embodiment of the present invention.
Figure 7B:
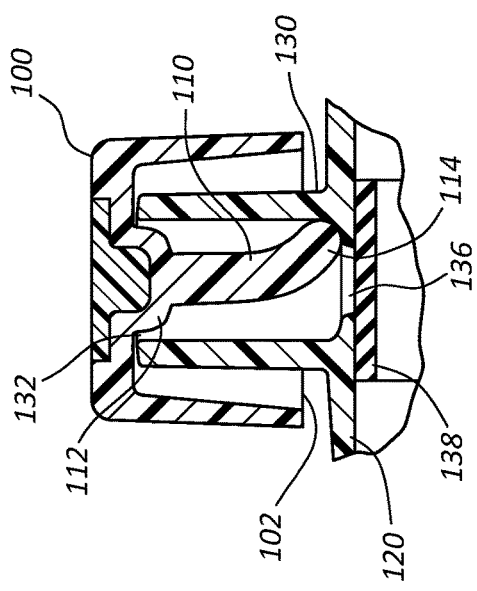

In other instances, distal end 114 further comprises a disc 116 having an increased diameter that is slightly less than the diameter of bottom 136, as shown in FIGS. 7A and 7B. Disc 116 increases the overall surface area of plug 110 without disturbing the normal function of the hinged cap. In some instance, disc 116 is positioned within bottom 136 when cap 100 is seated onto side port 130. Thus, the increased surface area of disc 116 is positioned within the location of internal volume 134 that is most likely to contain residual fluid. In some instances, the process of advancing disc 116 into bottom 136 displaces residual fluid from bottom 136, whereby the majority of space at bottom 136 is occupied by the antimicrobial disc 116.

Figure 8:
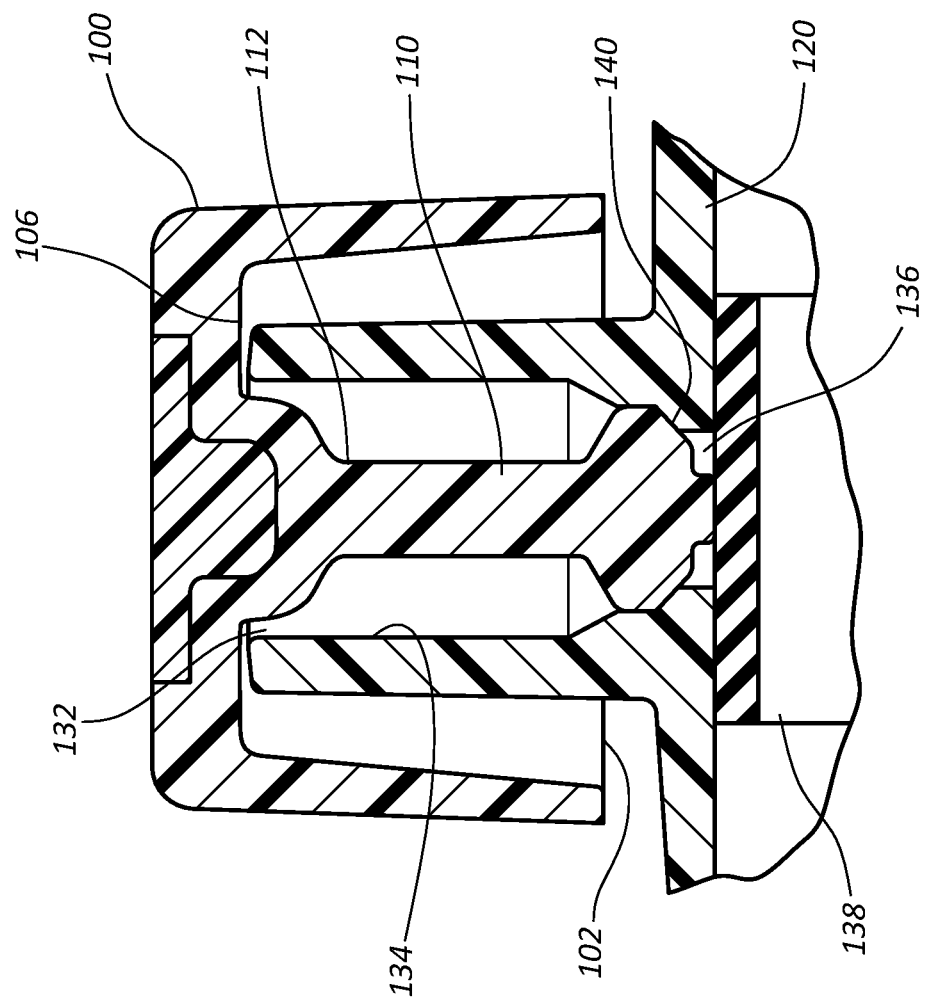
FIG. 8 shows a cross-section view of an antimicrobial plug having a three-dimensional terminal end shape that is the same as the internal geometry of the side port in accordance with a representative embodiment of the present invention.
Figure 9C:
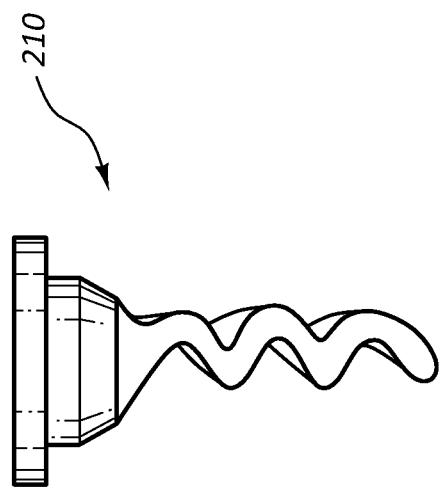
FIG. 9, shown in parts A-D, shows various views of a removable antimicrobial plug in accordance with various representative embodiments of the present invention.
Figure 9D:
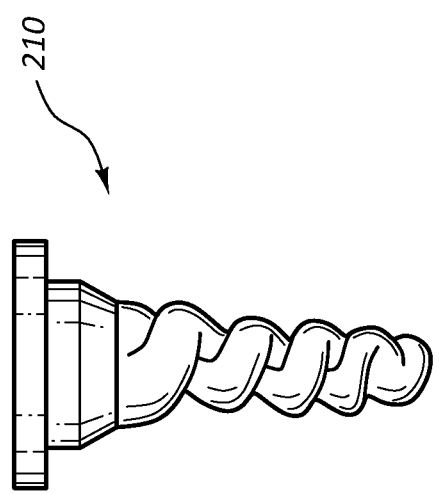

In some embodiments, internal volume 134 comprises a unique, internal geometry 140 having various surfaces, as shown in FIG. 8. Maximum antimicrobial effects may thus be achieved by shaping distal end 114 to have the same geometry as internal geometry 140. Thus, distal end 114 achieves maximum surface contact with internal geometry 140, thereby imparting maximum antimicrobial effect to internal volume 134.

Some implementations of the present invention further comprise a cap 200 having a hole 220 in the cap's base 216, as shown in FIGS. 9A and 9B. Hole 220 comprises a diameter configured to receive a removable and/or disposable antimicrobial plug 210. Plug 210 comprises materials and characteristics similar to the other antimicrobial components and devices previously described herein.

Cap 200 is assembled by inserting distal end 214 into and through hole 220 until proximal end 212 is fully seated into recess 217 of base 216, as shown in FIG. 9B. In some instances, the shaft portion of antimicrobial plug 210 comprises a diameter that is slightly larger than the diameter of hole 220, thereby facilitating a fluid-tight, interference fit between the two components. Antimicrobial plug 210 may subsequently be removed from cap 200 and replaced with a new plug once the antimicrobial properties of the initial plug 210 are exhausted. In other instances, antimicrobial plug 210 is replaced at a controlled frequency for maintained antimicrobial effects.

In some embodiments, multiple antimicrobial plugs are provided from which a user may select and insert into hole 220. For example, in some instances a plurality of plugs are provided, wherein each plug comprises a unique or different antimicrobial agent. Antimicrobial plug 210 may also comprise various non-linear shapes, such as a spiral shape or wavy shape, as demonstrated in FIGS. 9C and 9D. These shapes increase the overall surface area of plug 210 without disturbing the normal function of cap 200, as discussed previously. The plug 210 may have a non-circular cross-sectional shape that varies from the proximal end to the distal end.

Some implementations of the present invention further comprise a cap 300 comprising a base surface 316 on which is providing a dehydrated antimicrobial material 380, as shown in FIG. 10A. The dehydrated antimicrobial material 380 comprises a material that swells and grows when exposed to residual fluids located within the internal volume of side port 130. For example, in some instances dehydrated antimicrobial material 380 comprises an open-cell, non-woven sponge material. In other instances dehydrated antimicrobial material 380 comprises a hydrogel.

Material 380 further comprises an antimicrobial agent 320, or an antimicrobial coating comprising an antimicrobial agent that is dissolved or eluted when material 380 is exposed to residual liquid 32, thereby swelling or undergoing an expansive growth, as shown in FIG. 10B. In some instances, material 380 resumes its original conformation upon removal of residual liquid 32. In other instances, a change in the size of material 380 indicates the presence of residual fluid 32, thereby alerting a clinician to replace cap 300 with a new cap.

Figure 11A:
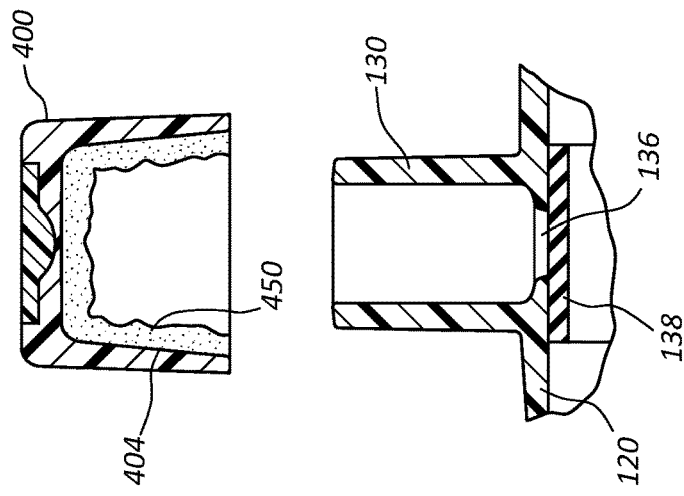
FIG. 11, shown in parts A-C, shows cross-section views of a cap having an antimicrobial lubricant applied to the inner surface of the cap in accordance with a representative embodiment of the present invention.
Figure 11B:
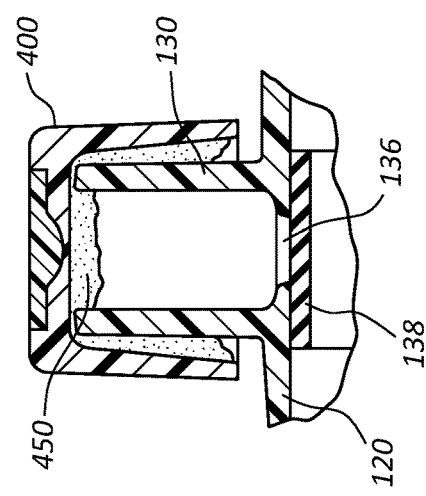
Figure 11C:
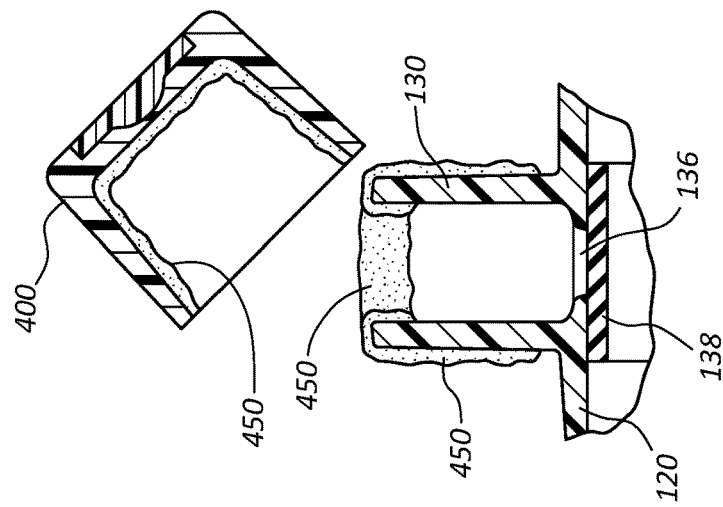

Further, in some instances the inner surface 404 of cap 400 comprises an antimicrobial lubricant 450, as shown in FIGS. 11A-11C. Antimicrobial lubricant 450 comprises a viscous or semi-viscous lube or gel having an antimicrobial agent that kills microbes that come in contact with the lubricant 450. In some instances, antimicrobial lubricant 450 comprises a mixture of chlorhexidine acetate, or chlorhexidine gluconate, and silicone.

A portion of antimicrobial lubricant 450 is transferred to the outer and inner surfaces of side port 130 as cap 400 is placed onto side port 130, as shown in FIG. 11B. Upon removal of cap 400 from side port 130, residual antimicrobial lubricant 450 remains on the inner surfaces of cap 400, and on the inner and outer surfaces of side port 130, as shown in FIG. 11C.

One having skill in the art will appreciate that the various other embodiments of the present invention may similarly be coated with an antimicrobial lubricant, thereby further adding a contact kill effect to the device. Thus, the features of the various embodiments of the present invention may be interchangeably implemented to provide a wide variety of antimicrobial caps and other devices.

Various embodiments of the present invention may be manufactured according to know methods and procedures. In some instances, an antimicrobial component is comprises of an antimicrobial material. In other instances, an antimicrobial component is extruded or molded of base polymer materials that have good bond strength to an antimicrobial material or agent, such as polycarbonate, copolyester, ABS, PVC, and polyurethane. The base polymer structure may be coated with an adhesive-based antimicrobial material, which may have elution characteristics. In some instances, the topology and dimensions of the base polymer structure are optimized for microbiology efficacy, lasting elution profiles, and assembly geometry constraints.

Various antimicrobial components of the instant invention may be casted or molded directly of antimicrobial material. In some instances, the antimicrobial component is casted in plastic and subsequently coated with an antimicrobial material. In some embodiments, an antimicrobial component is grown directly onto another component of the device. For example, in some instances an antimicrobial plug is grown directly from the inner or base surface of the cap. This is done by first placing a peel-away sleeve on the base surface of the cap. The antimicrobial material is deposited into the lumen formed by the sleeve. After curing is complete, the sleeve is peeled away, thereby revealing the plug on the base surface of the cap.

In other instances, various components of the device are joined together via an adhesive or epoxy. For example, in some instances an antimicrobial plug is initially casted or molded, and then coated with an antimicrobial coating or material. The coated plug is then adhered to the base surface of the cap by an epoxy. For the disc-end antimicrobial plugs, the disc and the rod or tube may be cast as a whole piece, or may be case or molded separately and then subsequently bonded together.

Antimicrobial components and coatings of the instant invention may be comprised of one or multiple antimicrobial agents in a polymer matrix. The polymer matrix may be adhesive-based, with a preference to acrylate- or cyanoacrylate-based adhesives for good bond strength and fast elution rates. Solvents may be added to increase bonding. Non-limiting examples of suitable antimicrobial material compositions are provided in United States Published Patent Application Nos. 2010/0137472, and 2010/0135949, each of which is incorporated herein by reference in their entireties.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An antimicrobial system, comprising:
 a catheter adapter having a proximal end, a distal end, an interior lumen disposed between the proximal end of the catheter adapter and the distal end of the catheter adapter, and a catheter extending from the distal end of the catheter adapter;
 a connector comprising a side port coupled to the catheter adapter, the connector having an upper aperture, a bottom proximate the interior lumen of the catheter adapter, and an internal volume between the upper aperture and the bottom, the side port being disposed between the proximal and distal ends of the catheter adapter; and
 an antimicrobial cap device comprising:
  a first end configured to secure the antimicrobial cap device to the connector, the first end having an opening sized to receive at least the upper aperture of the connector;
  a base;
  one or more sidewalls connecting the base to the first end, one or more inner surfaces of the one or more sidewalls defining a volume sufficient to receive at least the upper aperture of the connector, wherein while the antimicrobial cap device is secured to the connector, the antimicrobial cap device and a portion of the connector form a closed volume comprising the internal volume of the connector; and
  an antimicrobial plug having a proximal end attached to the base and a distal end disposed outwardly therefrom, wherein the distal end of the antimicrobial plug comprises a disc having a diameter that is greater than a diameter of the antimicrobial plug along a length of the antimicrobial plug between the proximal end of the antimicrobial plug and the distal end of the antimicrobial plug, wherein the disc and the proximal end of the antimicrobial plug are is monolithically formed as a single unit;
 wherein the catheter adapter comprises a port valve disposed within the interior lumen of the catheter adapter, and the port valve forming a seal between the side port and the interior lumen of the catheter adapter, wherein the port valve selectively blocks fluid communication between the catheter adapter and the side port through the bottom of the connector, wherein upon injecting a fluid into the side port, the port valve is temporarily defeated to permit the fluid to bypass the port valve and enter the interior lumen of the catheter adapter; and
 the distal end of the antimicrobial plug extends through the bottom to abut the port valve when the antimicrobial cap device is secured to the connector.

2. The device of claim 1, further comprising a hole in the base of the antimicrobial cap device, wherein the distal end of the antimicrobial plug is inserted through the hole and the proximal end of the antimicrobial plug seals the hole.

3. The device of claim 1, wherein the distal end of the antimicrobial plug comprises a three-dimensional shape having a same internal geometry as a portion of the connector.

4. The device of claim 1, wherein the antimicrobial plug comprises at least one of a rod and a tube.

5. The device of claim 1, wherein the antimicrobial plug comprises an antimicrobial material.

6. The device of claim 1, wherein the antimicrobial plug comprises a polymer matrix in which is evenly dispersed an antimicrobial agent.

7. The device of claim 6, wherein the antimicrobial agent is eluted from the polymer matrix when the antimicrobial plug is contacted by the fluid.

8. The device of claim 1, wherein cross-sectional shapes of the antimicrobial plug are different one from another at the proximal end of the antimicrobial plug, at the distal end of the antimicrobial plug, and along the length thereof between the proximal end of the antimicrobial plug and the distal end of the antimicrobial plug.

9. The device of claim 1, wherein the disc, the one or more sidewalls, and the proximal end of the antimicrobial plug are monolithically formed as a single unit.

10. An antimicrobial cap device for a connector in fluid communication with a medical device, the connector having an upper aperture, a bottom, and an internal volume, the antimicrobial cap device comprising:
- a first end configured to secure the antimicrobial cap device to the connector, the first end having an opening sized to receive at least the upper aperture of the connector;
- a base;
- one or more sidewalls connecting the base to the first end, one or more inner surfaces of the one or more sidewalls defining a volume sufficient to receive at least the upper aperture of the connector, wherein while the antimicrobial cap device is secured to the connector, the antimicrobial cap device and a portion of the connector form a closed volume comprising the internal volume of the connector; and
- an antimicrobial plug having a proximal end attached to the base and a distal end disposed outwardly therefrom, the antimicrobial plug comprising a curved shape along a length thereof from the proximal end of the antimicrobial plug to the distal end of the antimicrobial plug, wherein a distal end of the curved shape is laterally offset from the proximal end of the antimicrobial plug such that the distal end of the curved shape is curved towards the one or more sidewalls when the antimicrobial cap device is freestanding, wherein the distal end of the curved shape is the distal end of the antimicrobial plug.

* * * * *